United States Patent [19]
Salyer

[11] Patent Number: 5,282,994
[45] Date of Patent: *Feb. 1, 1994

[54] DRY POWDER MIXES COMPRISING PHASE CHANGE MATERIALS

[75] Inventor: Ival O. Salyer, Dayton, Ohio

[73] Assignee: The University of Dayton, Dayton, Ohio

[*] Notice: The portion of the term of this patent subsequent to Apr. 21, 2009 has been disclaimed.

[21] Appl. No.: 870,487

[22] Filed: Apr. 16, 1992

Related U.S. Application Data

[63] Continuation-in-part of Ser. No. 462,365, Jan. 9, 1990, Pat. No. 5,106,520.

[51] Int. Cl.$^5$ .............................................. C09K 5/06
[52] U.S. Cl. .................................... 252/70; 524/5; 524/8; 524/493; 428/402; 428/403
[58] Field of Search .................. 252/70; 165/10 A; 428/306, 403; 524/8

[56] References Cited

U.S. PATENT DOCUMENTS

| | | | |
|---|---|---|---|
| 3,603,106 | 9/1971 | Ryan | 252/70 |
| 3,823,089 | 7/1974 | Ryan | 62/457 |
| 3,977,202 | 8/1976 | Forusz | 62/4 |
| 3,980,070 | 9/1976 | Krupa | 126/263 |
| 4,003,426 | 1/1977 | Best | 165/53 |
| 4,008,170 | 2/1977 | Allan | 252/69 |
| 4,182,398 | 1/1980 | Salyer | 165/1 |
| 4,205,685 | 6/1980 | Yoshida | 52/173 |
| 4,237,023 | 12/1980 | Johnson et al. | 252/70 |
| 4,253,983 | 3/1981 | Blanie | 252/70 |
| 4,259,198 | 3/1981 | Kreibich | 252/70 |
| 4,259,401 | 3/1981 | Chahroudi et al. | 428/306 |
| 4,273,667 | 6/1981 | Kent | 252/70 |
| 4,292,189 | 9/1981 | Chen | 62/59 |
| 4,294,078 | 10/1981 | MacCracken | 62/59 |
| 4,367,788 | 1/1983 | Cordon | 165/53 |
| 4,463,799 | 8/1984 | Takahashi | 165/10 |
| 4,470,917 | 9/1984 | Hawe | 252/70 |
| 4,504,402 | 3/1985 | Chen | 427/212 |
| 4,505,953 | 3/1985 | Chen | 252/70 |
| 4,513,053 | 4/1985 | Chen | 428/221 |
| 4,545,916 | 10/1985 | Chalk | 252/70 |
| 4,561,989 | 12/1985 | Wada | 252/70 |
| 4,567,877 | 2/1986 | Sepahpur | 126/246 |
| 4,617,332 | 10/1986 | Salyer et al. | 524/4 |
| 4,668,564 | 5/1987 | Orchard | 428/246 |
| 4,671,267 | 6/1987 | Stout | 128/156 |
| 4,680,173 | 7/1987 | Burger | 424/47 |
| 4,711,813 | 12/1987 | Salyer | 428/402 |
| 4,747,240 | 5/1988 | Voisinet | 52/173 |
| 4,797,160 | 1/1989 | Salyer | 106/56 |
| 4,851,291 | 7/1989 | Vigo | 428/393 |
| 4,908,166 | 3/1990 | Salyer | 264/22 |
| 4,964,402 | 10/1990 | Grim | 128/80 H |
| 5,053,446 | 10/1991 | Salyer | 524/8 |
| 5,106,520 | 4/1992 | Salyer | 252/70 |

FOREIGN PATENT DOCUMENTS

| | | |
|---|---|---|
| 022717 | 3/1979 | European Pat. Off. |
| 2643895 | 3/1978 | Fed. Rep. of Germany |
| 3045842 | 7/1980 | Fed. Rep. of Germany |
| 197806 | 4/1981 | France |
| 42380 | 8/1968 | Japan |
| 86191 | 5/1969 | Japan |
| 86188 | 4/1970 | Japan |
| 170180 | 11/1970 | Japan |
| 142276 | 6/1971 | Japan |
| 232164 | 3/1976 | Japan |

OTHER PUBLICATIONS

Advanced Phase Change Materials for Passive Solar Storage Applications Salyer et al. 1985 Soc. of Automotive Engineers 859008 Aug. 1985.

Intersol 85 Proceedings of the 9th Biennial Congress of the Int'l Solar Energy Society, Bilgen and Hollands.

Primary Examiner—Paul Lieberman
Assistant Examiner—Necholus Ogden
Attorney, Agent, or Firm—Killworth, Gottman, Hagan & Schaeff

[57] ABSTRACT

Free flowing, conformable powder-like mix of silica particles and a phase change material (PCM) is provided. The silica particles have a critical size of about 0.005 to about 0.025 microns and the PCM must be added to the silica in an amount of 75% or less PCM per combined weight of silica and PCM. The powder-like mix can be used in tableware items, medical wraps, tree wraps, garments, quilts and blankets, and in cementitious compositions of the type in which it is beneficial to use a PCM material. The silica-PCM mix can also be admixed with soil to provide a soil warming effect and placed about a tree, flower, or shrub.

10 Claims, 2 Drawing Sheets

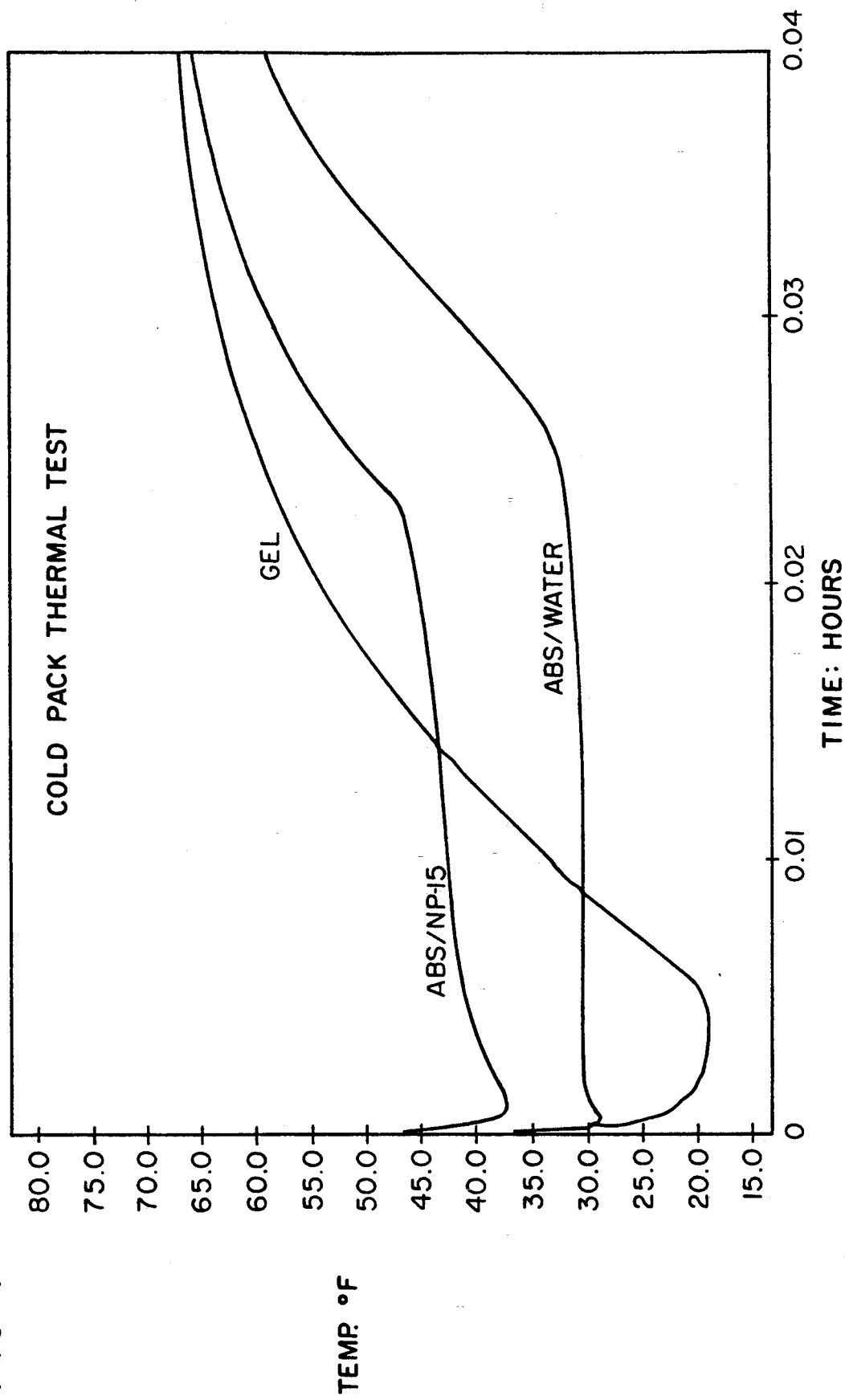

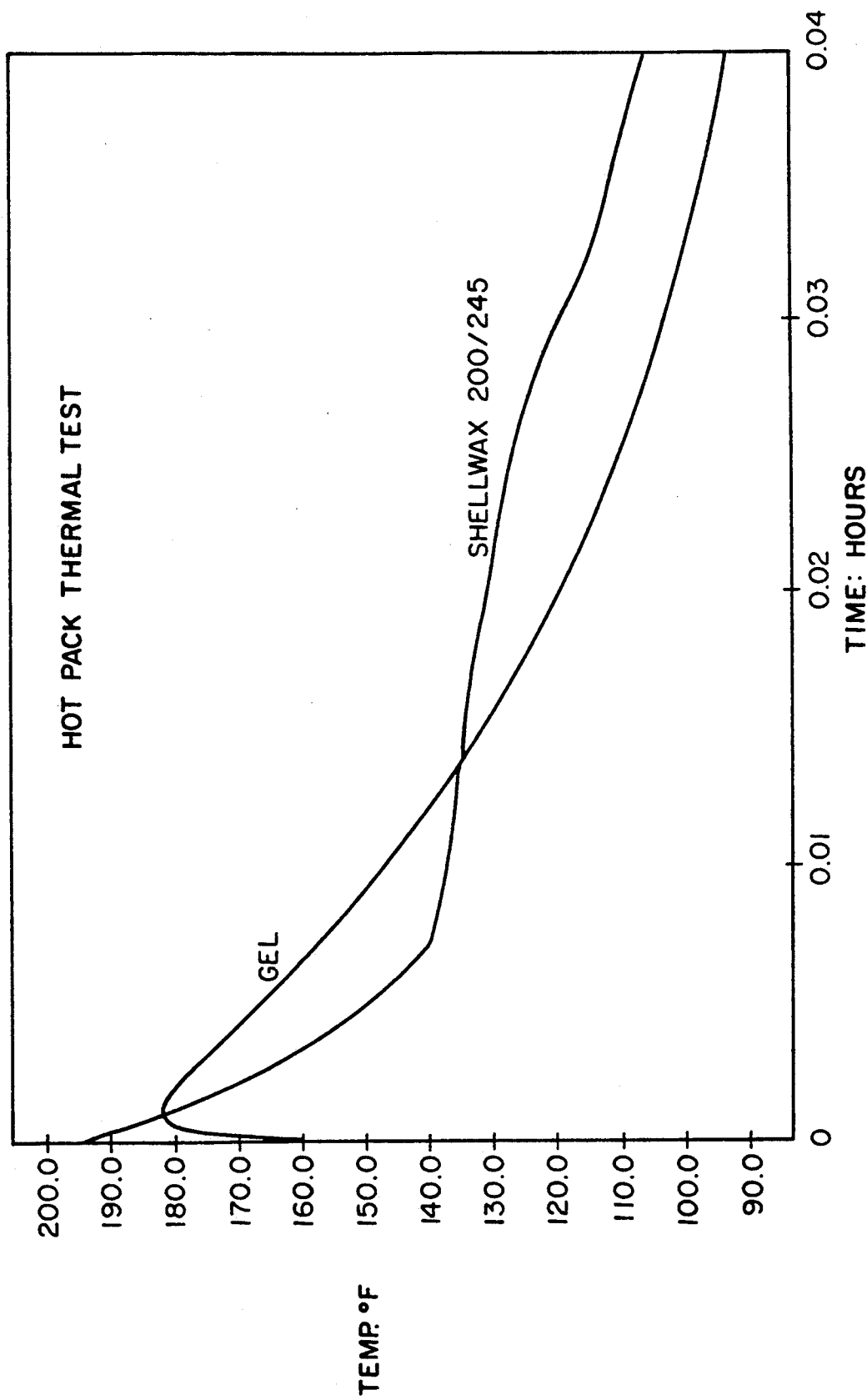

DRY POWDER MIXES COMPRISING PHASE CHANGE MATERIALS

GOVERNMENT RIGHTS

The Government has rights in this invention pursuant to Contract No. DE-FG03-86SF16308 awarded by the U.S. Department of Energy.

RELATED APPLICATIONS

This application is a continuation-in-part of Ser. No. 462,365, filed Jan. 9, 1990, now U.S. Pat. No. 5,106,520, issued Apr. 21, 1992, the disclosure of which is hereby incorporated by reference. Reference is also made to related application Ser. No. 835,854, now U.S. Pat. No. 5,211,949, issued May 18, 1990 filed Feb. 18, 1992 as a divisional of Ser. No. 462,365.

BACKGROUND OF THE INVENTION

The present invention relates to a dry, freely flowing powder mix comprising a phase change material.

Phase change materials may be repeatedly converted between solid and liquid phases and utilize their latent heat of fusion to absorb, store and release heat or cool during such phase conversions.

These latent heats of fusion are greater than the sensible heat capacities of the materials. For example, in phase change materials, the amount of energy absorbed upon melting or released upon freezing is much greater than the amount of energy absorbed or released upon increasing or decreasing the temperature of the material over an increment of 10° C.

Upon melting and freezing, per unit weight, a phase change material (PCM) absorbs and releases substantially more energy than a sensible heat storage material that is heated or cooled over the same temperature range. In contrast to a sensible heat storage material that absorbs and releases energy essentially uniformly over a broad temperature range, a phase change material absorbs and releases a large quantity of energy in the vicinity of its melting/freezing point.

Phase change materials capable of storing and releasing thermal energy have found many applications in building structures, road base materials, beverage and food containers, medical wraps, and textile applications such as garments. One of the basic problems, however, in the use of solid-to-liquid PCM's for control of temperature, is containment. That is, for heat transfer efficiency as well as safety purposes, it is undesirable to have a thick block or agglomeration of solid phase PCM below the PCM melting point. Similarly, when above the melting point, PCM in liquid phase can be problematic. For instance, building panels containing liquid phase PCM have proven deficient. In one such PCM-containing panel, carpenters reported that a liquid phase PCM leaked out of the panel when nails were driven through it.

In those situations in which medical hot or cold packs containing PCMs are used, a solid phase agglomerate of PCM below its melting point renders the structure unwieldy and incapable of conforming about the required body part to achieve the desired heating or cooling function.

Accordingly applicant has developed a series of PCM containment systems. These are represented by U.S. Pat. Nos. 4,617,332, 4,711,813, 4,797,160, 4,908,166, and 5,053,446, all assigned to the same assignee as the present invention. However, none of the containment means disclosed in those patents involve silica. Still, the broad idea of using silica as a suspension medium for PCMs in building blocks is not new. For instance, see U.S. Pat. No. 4,259,401 (Charoudi et al) wherein this concept is disclosed at column 21, line 60 et seq. Also, Johnson et al in U.S. Pat. No. 4,237,023 discloses incorporating fumed silicon dioxide with inorganic phase-change salts which are capable of forming salt hydrates in the presence of water and Chang in U.S. Pat. No. 4,292,189 discloses a phase change energy storage system based on a combination of two inorganic salts together with nucleating and thickening agents including silicas. Finally, Allen, U.S. Pat. No. 4,008,170 describes a powdered product prepared by the vapor phase hydrolysis of a silicon compound reacted with liquid water. However, the dry water in Allen is not used as a phase change material for the storing and releasing of thermal energy.

Besides, the prior art does not suggest utilization of the combination of the preferred silica having the recited particle size and the PCM/silica weight ratios herein required in order to result in a dry, conformable, powder-like, PCM containing composition that may be useful in widespread environments.

Accordingly, it is an object of the invention to provide a conformable, powder-like PCM-matrix composite that will not liquefy upon heating of the PCM above its melting point and will not form a rigid solid at temperatures below the melting point. In other words, it is desirable to find a new method of containment for the PCM wherein, when above or below its melting point, the PCM-matrix structure will be in the form of a soft, conformable configuration like a sand pack.

SUMMARY OF THE INVENTION

That object is met by the present invention which provides a novel phase change material/silica dry powder composite. The phase change material (PCM) may consist of one or more of the following compositions: water, salt hydrates, quaternary ammonium halide clathrates, linear alkyl hydrocarbons, fatty acids, alcohols and esters, glycerine, pentaerythritol, pentaglycerine, neopentylglycol, polyethylene glycol and like materials characterized by having thermal energy storage of 30 calories/gram or higher, and a narrow temperature range of melting and freezing.

The silicas that are suitable include those made by the fumed or precipitated process, and having surface areas ranging from 50 to 500 square meters per gram, and primary particle sizes from 0.005 to 0.025 microns. Preferred silicas are those having a surface area of 100 $m^2$ per gram or more, and primary particle size of 0.020 microns or less. Further, the silicas prepared by either the fumed or precipitated process can be modified to make them less hydrophilic, or even hydrophobic by surface treating them with effective concentrations of silane coupling agents (e.g., dimethyldichlorsilane) or silicone resins. The silicone resin surface treatment can and usually is followed by heat treating at elevated temperature wherein the silicone resin is chemically reacted with hydroxyl groups on the surface of the silica particles. Importantly, controlled degrees of hydrophobic character can be obtained by varying the amount of waterproofing agent. This precisely tailored balance of hydrophobic/hydrophilic character is very important in the preparation of PCM/silica dry powders using quaternary ammonium halides, and salt hydrates in order to diminish the attraction of the hydroxyl and other polar groups on the silica for the water molecules in these types of PCMs.

When water is used as the PCM, it has been found that while normal hydrophilic fumed silica can be used to form a dry powder with a PCM at the silica/water (40/60) concentration by weight, the preferred silica is a precipitated silica. The precipitated silicas are preferred over the fumed silicas for making the PCM/silica dry powders for several reasons. For example, the precipitated silicas sell for about 1/5 the price of the corresponding fumed silica, and the precipitated silicas have less tendency to tie up water molecules, thus providing higher thermal energy storage in water/silica dry powder. This dry powder remains soft and conformable above and below the melting temperature of water/ice. A water/silica dry powder is also lower in cost and is non-burning. There are many thermal energy storage applications for a water/silica dry powder in food servingware (to keep food cold) and in medical wraps (cold therapy).

As mentioned, it has been found that a very small size silica filler is be used as a matrix for the PCM. This silica filler has particle sizes on the order of about 0.005 to 0.025 microns in diameter and is capable of absorbing five to ten times its weight of liquid PCM. The silica filler is literally stirred into the liquid PCM at a temperature that is above the melting point of the PCM. At combinations of PCM/silica filler of 90/10–85/15 (weight) a gel composition is obtained. However, when mixed at 75/25 PCM/silica filler and at lower PCM content, a free-flowing powder is obtained that remains free flowing above and below the melting temperature of the PCM. This type of structure is especially desirable for hot and cold medical wrap applications, but is of interest in other applications such as for citrus tree wraps, tableware, building structures, soil admixtures, garments, blankets, quilts, etc.

The preferred addition range for the PCM is from about 75%–50% (by weight based upon total weight of the composite, i.e., silica-PCM mixture). For convenience in mixing, the dry silica are usually added to liquid PCM (i.e., PCM maintained at a temperature higher than its melting point). However, the reverse addition of PCM to silica can also be accomplished with suitable equipment to prevent aerosolization of the finely divided silica.

In those situations in which the PCM/silica mix is to be used as a hot medical wrap, it is desirable to provide a microwavable package containing the mix. To enhance this capacity, polar additives may be added to the mix to absorb microwave energy effectively or the PCM itself may be a polar compound such as high molecular weight (i.e., $\geq 1,000$) polyethyleneglycol material.

A variety of different PCM materials may be used in the silica-PCM mixture as long as the melting and freezing temperatures thereof fall within a broad range of between about $-20°$ to about $140°$. The lower melting PCMs are useful for medical therapy cold pack, citrus tree frost protection and soil admixtures, with the higher melting PCMs being useful for medical therapy heat packs, tableware, etc. It is preferred that the PCM have a latent heat of fusion of about 30 cal./gram or higher.

In accordance with the invention, a dry powder-like PCM-silica mix is provided that may be used for: medical hot and cold pack applications, as a wrap for citrus trees, or in admixture with soil to protect trees or plants implanted therein, building structure applications such as in plasterboard, and food and tableware accessory items, and in garments, blankets, etc.

BRIEF DESCRIPTION OF THE DRAWINGS

FIG. 1 is a graph of temperature versus time for the three test specimens of Example 5.

FIG. 2 is a graph of temperature versus time for the two test specimens of Example 7.

DETAILED DESCRIPTION OF THE PREFERRED EMBODIMENT

In accordance with the above, it is apparent that the ultrafine particle size silica provides a convenient carrier for the PCM. The fact that the PCM-silica powder mix readily conforms to different shapes is of benefit when the mix is used as a medical hot or cold pack. The dry blend minimizes PCM leakage problems that may otherwise occur. Use of hydrophobic silica in combination with non-polar PCM provides solution to a phase separation problem otherwise encountered in high humidity environments or on exposure of the dry powder to liquid water.

As mentioned, the particle size of the silica is critical. Sub-micron, ultra fine particle size silicas on the order of about 0.005 to about 0.025 microns (in diameter) can be manually mixed in a solution of phase change material within a critical addition range. That is, the ultrafine silica should be added to the phase change material to produce a mixture having about 75% PCM (weight PCM based on total weight of PCM and silica in mix) or less. If more than about 75% of the PCM is added, a gel-like mixture is provided. However, at about 75/25 PCM:silica, a free-flowing powder is obtained that remains free-flowing both above and below the melting temperature of the PCM. This type of structure is especially desirable for hot and cold medical wraps, but is of interest for other applications as well (such as in citrus tree wraps, tableware, garments, blankets).

While as set forth in parent application Ser. No. 462,365, sub-micron particle size silicas made by either of two different processes (i.e. either fumed silica made by hydrolysis of silicon tetrachloride vapor in a hydrogen/oxygen flame or precipitated silica made from an alkaline silicate such as sodium silicate that is precipitated with a mineral acid or metal salt) may be used, it has now been determined that either a precipitated silica or a surface treated precipitated silica is preferred depending on the PCM used and the use to which the dry powder is put.

Thus a preferred silica is a precipitated hydrophilic silica having a particle size of 0.005 to 0.025 microns and a surface area of 100 $m^2$ per gram or more. An example is ABS silica from PPG Industries of Pittsburgh, Pa., which is a normal, hydrophilic silica with a surface area of 150 $m^2$/gram and a particle size of about 0.022 microns.

Alternatively, the preferred silica is a precipitated hydrophilic silica of the same type that has been further surface treated to render it less hydrophilic, partially hydrophobic, or hydrophobic. Preferably the silica is treated with 1–15 pph (parts per hundred by weight) of a silane coupling agent such as dimethyldichlorosilane or silicone resin. The preferred degree of hydrophobic character depends on the type of PCM being used. For example, with water as the phase change material, the silica should be completely hydrophilic or only slightly (i.e. around 1 pph) waterproofed by surface treatment. When the phase change material is a quaternary ammonium halide or a salt hydrate or when a non-water PCM/silica dry powder is to be used in a moist environment (i.e. where phase separation can occur quickly as the silica preferentially absorbs water and absorbs the non-water PCM), then a less hydrophilic, partially hydrophobic, or hydrophobic silica is preferred.

Other than the above-mentioned preferences on the types of silica used with certain PCM's and depending on certain uses to which the dry powder is put, all of the silicas mentioned in parent application Ser. No. 462,365 may be used. Likewise, all of the PCM's mentioned in parent application Ser. No. 462,365 may be used.

In parent application, crystalline alkyl hydrocarbons having a chain length of $C_{14}$ and greater where indicated to be the preferred PCM for most situations. While such alkyl hydrocarbons remain preferred for a number of situations, recently water/silica dry powders have gained emphasis for a number of uses including ice packs (in place of cold gel packs), food servingware (to keep cold food cold) and in medical wraps (cold therapy). A water/silica dry powder of the type disclosed herein has an excellent capability of storing and releasing thermal energy within the temperature range preferred for ice packs, food servingware and medical wraps, is the lowest cost dry powder, and remains soft and conformable above and below the melting temperature of water/ice.

As to the other PCM's that may be used, suitable clathrates include those which consist of either a nobel gas (i.e., the gas clathrates) or a non-polar halocarbon which forms hydrates in as little as 10% concentration. The chlorofluorocarbon clathrates tend to be relatively expensive and are, therefore, not preferred. Additionally, some specific chlorofluorocarbons (e.g., Freon 11, 12, etc) are also suspected to contribute to depletion of the earth's ozone shield and are undesirable for this reason as well.

Promising clathrate PCMs include the quaternary amine salts with halogen or other acids (clathrates or semi-clathrates) These hydrates are pseudo compounds, wherein the crystals of "ice" are able to host organic molecules (of specific composition) in nearly spherical cages of two different sizes. If only the larger of the two cages is occupied by the guest molecules, the PCM may contain 33 or more molecules of water. If both cages are occupied by guest molecules, the PCM will contain about 17 molecules of water. In either case, the water content in these clathrate and semi-clathrate PCMs is much higher than in some of the salt hydrates such as sodium sulfate decahydrate.

Nearly all hydrated salts can be employed, with various degrees of suitability, as PCM. The only such materials which are wholly unsuitable are those which decompose, rather than melt. Marginally suitable hydrated salts are those which melt incongruously, those with low heats of fusion, and those with melting points which lie outside (generally far above) desired temperature ranges. Nevertheless, there are a wide variety of meltable hydrated salts with high heat of fusion and useable melting points; and many of these satisfy stringent cost requirements. The preferred hydrated salts are those which are formed primarily from the combination of positive ions of sodium, potassium, calcium, ammonium and iron with negative ions of acetate, silicate, chloride, nitrate, mono, di, and tri basic phosphate, mono and di basic carbonate and mono and di basic sulphate. Other ions may be added to the above compositions in small quantities (although they are more expensive) in order to adjust melting point or to obtain other desired properties. Virtually all such combinations will function in the desired manner; and most have melting points in the useful range, for example:

$Fe_2O_3.4SO_3.9H_2O$, $NaNH_4SO_4.2H_2O$, $NaNH_4HPO_4.4H_2O$, $FeCl_3.2H_2O$, $Na_3PO_4.12H_2O$, $Na_2SiO_3.5H_2O$, $Ca(NO_3)_2.3H_2O$, $K_2HPO_4.3H_2O$, $Na_2SiO_3.9H_2O$, $Fe(NO_3)_3.9H_2O$, $K_3PO_4.7H_2O$, $NaHPO_4.12H_2O$, $CaCl_2.6H_2O$ and $Na_2SO_4.10H_2O$, $Na(CH_3COO).3H_2O$.

The specific melting point desired is obtained by varying the degree of hydration and by alloying it to form binary or trinary eutectics.

As above noted, the crystalline alkyl hydrocarbons having a carbon chain of about 14 carbon atoms or greater are preferred in some instances. These waxes are commercially available under a host of trademarks. For instance, these commercially available waxes include: Shellwax ® 100 (MP 42°–44° C.), Shellwax ® 120 (MP 44°–47° C.), Shellwax ® 200 (MP 52°–55° C.), Shellwax ® 300 (MP 60°–65° C.) all of which are products of Shell Oil Co.; Boron R-152 (MP 65° C.) a product of Standard Oil of Ohio (SOHIO); Union SR-143 (MP about 61° C.) a product of Union Oil Co.; Witco 128 (MP about 53° C.) Witco LLN, Witco 45A, Witco K-61, Witco K-51, and Witco 85010-1 all products of Witco Corporation (Kendall Division); Aristowax ® 143 (MP34°–61° C.), and Paraffin 150 (MP about 61° C.).

These waxes have heats of fusion greater than 30 cal/g and by comparison to other phase change materials they are inexpensive.

One group of waxes for use in the present invention includes commercially available mixtures of crystalline alkyl hydrocarbons. These mixtures of alkyl hydrocarbons are obtained at low cost as by-products of petroleum refining. Typically, these are blends of alkyl hydrocarbons which differ by no more than 4 or 5 carbon atoms. A typical example is Witco 45A which contains about 21% C-18, 33% C-19, 26% C-20; 11% C-21 hydrocarbon, and the balance higher and lower hydrocarbons. Because they are inexpensive, they can be incorporated into the silica-PCM composite at minimal additional expense and, at the same time, provide high savings in terms of reduced energy costs.

While these waxes are mixtures they exhibit one melting and freezing point which is the average of the melting and freezing points of the constituents. Some blends for passive heating and cooling have a melting and freezing point in the range of 24° to 33° C. Some blends for passive cool storage have a melting and a freezing point in the range of 0° to 33° C. In many applications, the blends will be relied upon for both heating and cooling and will be characterized by having both the melting and a freezing point in the range of 20° to 25° C.

Ultra pure alkyl hydrocarbons C-14 to C-22 and higher are also available at a premium cost. These may have higher heats of fusion and crystallization (e.g., 55–60 cal/g) than the low-cost mixtures described above. These ultra pure alkyl hydrocarbons are also useful in the present invention for critical applications requiring maximum storage capacity in the minimum volume of space.

Another consideration in the selection used in the present invention is the difference between the melting and freezing points. The alkyl hydrocarbons are self-nucleating and thus melt and freeze congruently. Thus, when heated or cooled at rates of 2° C./min. or less, the melting and freezing temperatures substantially coincide. Additionally, the halogen terminated alkyl hydrocarbons can be useful as a PCM and also provide fire retardancy.

When the powder-like silica/PCM mixture is to be used for medical hot wrap applications, it is desirable to heat the mix via microwave or other dielectric heating means. In such cases, a polar PCM such as water, glycerine, ethylene glycol, a high molecular weight (i.e., greater than 1,000) polyethylene glycol, the clathrates, semi-clathrates, gas-clathrates and hydrates may be used.

Alternatively, if a microwavable product is desired, a non-polar PCM such as the crystalline long chain ($C_{14}$ and greater) alkylhydrocarbons, crystalline fatty acids, crystalline fatty acid esters, crystalline alicyclic hydrocarbons and crystalline aromatic hydrocarbons can be used provided they are used conjointly with polar compounds such as water, ethylene glycol, glycerine, polyethylene glycol, and Ivory liquid, etc. Such polar compounds should be added to the silica-PCM composite in an amount of from 5–25 weight percent, preferably 5–10 weight percent (based upon the total weight of the silica/PCM/polar compound combination).

The silica-PCM mix may also be enhanced by the use of an antioxidant in the formulation. Typically, the antioxidant will be needed only when the crystalline alkyl hydrocarbon PCM or a polar organic PCM such as ethylene glycol, polyethyleneglycol or glycerine is employed. The antioxidants should be added, when used, in an amount of from 0–1% (weight) based on the weight of the PCM. Exemplary antioxidants include the well-known hindered phenol materials and aromatic amines. Preferred antioxidants include BHA (butylated hydroxy anisole), Santowhite crystals (i.e., 4,4'-thiobis(6-tert-butyl-m-cresol) and Santowhite powder (i.e., 4,4'-isopropylidene bis(6-tert-butyl-m-cresol). The Santowhite products are available from Monsanto.

It is to be understood that thermal insulation materials such as polyurethane or polystyrene foam are desirably used to surround the shrouded PCM/silica composites in order to minimize undesirable heat loss or gain from the environment. For example, insulating materials would be used when the PCM/silica composites are used as medical wraps, tree wraps, tableware products, garments, blankets and the like. In each case, a layer of such thermal insulation would be provided so as to minimize heat loss or gain as the case may be.

In order that the invention may be more readily understood, reference is made to the following examples, which are intended to be illustrative of the invention, but are not intended to be limiting in scope.

EXAMPLE 1

This example illustrates the general laboratory procedure for preparing a water/silica dry powder thermal energy storage composition. One thousand grams of distilled water was placed into a mixing tray having the dimensions of about 14"×18"×5". The tray preferably comprises stainless steel, although porcelain or plastic trays may also be suitable. Since water is in the liquid state at room temperature it was not necessary to apply any heat to the mixing tray. However, for PCMs that melt above room temperature, the mixing tray was placed on a hot plate and heated to a temperature of about 25° C. above the melting temperature of the PCM.

From a preweighed lot, a commercially available precipitated hydrophilic silica from PPG Industries of Pittsburgh, Pa. (ABS silica) having a surface area of 150 $m^2$/gram and an ultimate particle size of about 0.022 microns was incrementally added to the distilled water with a putty knife while mixing and stirring. The ABS silica was readily wetted by the water PCM, and an increase in the viscosity of the water was noted after a water/silica 90/10 composition was achieved. Further addition of silica resulted in a loose gel at about water/silica 85/15 composition, and a stiff gel at about water/silica 80/20. The conversion of the stiff gel to the dry powder was achieved by adding more ABS silica and mixing the silica into the gel particles with a putty knife. Care must be taken to break up the gel particles as completely as possible by intensive manual mixing. A dry powder was obtained when sufficient ABS silica has been added to bring the composition to water/silica 70/30 or 60/40 range. Thus for a water/silica dry powder the preferred weight % of water is 60–70%. Optionally, after the dry powder has been formed, it may be screened through a 20 mesh screen to remove any large gel particles. These can be broken up manually and remixed into the balance of the dry powder.

Tests that are then run on the dry powder are apparent density, thermal energy storage, and cold conformability (the ability to retain the loose powder structure at a temperature below the freezing temperature of the PCM). The apparent density of the dry powder should be about 0.5 gm/cc. The thermal energy storage should be near that calculated from the thermal energy storage of the neat (100%) PCM, and multiplied by percent PCM in the dry powder. The conformable property is determined by placing the material in a freezer overnight and determining if the sample retains the free flowing characteristics that it has at ambient temperature.

An analysis of the thermal energy storage properties of water/ABS silica dry powder was conducted using a differential scanning calorimeter (DSC). In this test, a small sample was heated at a controlled rate (e.g., 2° C./minute) and the energy required to maintain the constant rate of temperature was monitored in comparison with a control blank. The extra electrical energy required to maintain the constant rate of heating and cooling becomes a direct measure of the energy of melting and freezing and is usually expressed in calories/grams. The exact location of the melting and freezing temperature is simultaneously located in this test, and the extent of supercooling (if present) is also measured. A differential scanning calorimeter analysis was run on a sample of distilled water/ABS silica dry powder PCM at a heating and cooling rate of 2° C./minute. The DSC data is shown in Table I below.

TABLE I

| Material | Tm °C. | Tc °C. | Tm-Tc °C. | ΔHf Cal/gm | Δhc Cal/gm |
|---|---|---|---|---|---|
| H₂O/ABS | 0.91 | −3.47 | 4.38 | 40.81 | 38.26 |
| H₂O/ABS | 0.88 | −3.47 | 4.35 | 37.75 | 34.65 |

An application test of the water/ABS silica dry powder was also performed wherein the time versus temperature of 300 grams samples of water/ABS silica dry powder, and a 15 carbon alkyl hydrocarbon from EXXON of Houston, Tex. (NP-15)/ABS silica dry powder, and a commercial water gel cold pack were measured. Samples of the three cold packs were placed on a counter top, thermocouples placed underneath each, and the time versus temperature recorded. It was readily apparent that the water/ABS silica dry powder, and the NP-15/ABS silica dry powder both provide a plateau of stable temperature near the respective temperatures of the Tc for more than 2 hours. On the other hand, the water gel had no temperature plateau and only showed a continuing thermocline from 32° F. toward room temperature.

EXAMPLE 2

The procedure described in Example 1 was used to prepare a water/silica dry powder using ordinary tap water and a low-salt precipitated silica from PPG Industries of Pittsburgh, Pa. (BXS-317) having a 0.022 microns particle size and a surface area of 150 m$^2$/gram. A stiff gel was obtained at water/silica 70/30, and a free flowing dry powder (that remained free flowing and conformable below 0° C.) at water/silica 67.8/32.2 composition. Tests of apparent density and thermal energy storage were also done and found to be at the predicted values. Several other PPG hydrophilic silicas were also successfully used to prepare water/silica PCM dry powders using the procedure described in Example 1. A summary of the DSC data is shown below in Table 2.

TABLE 2

| Material | Tm °C. | Tc °C. | Tm-Tc °C. | AHf Cal/gm | Ahc Cal/gm |
|---|---|---|---|---|---|
| H$_2$O/BXS-317 (67.8/32.2) | 0.6 | −7.44 | 8.04 | 44.83 | 42.84 |
| H$_2$O/BXS-317 (67.8/32.2) | 0.6 | −7.52 | 8.12 | 44.32 | 42.08 |

EXAMPLE 3

A series of three surface treated silicas were prepared by PPG Industries by surface coating silica particles with silicone resin at 1 pph (BXS-318), 3 pph (BXS-319) and 5 pph (BXS-320). All were precipitated silicas having a particle size in the range of 0.022 microns and a surface area of 99-126 m$^2$/gram. Using the procedure described in Example 1, attempts were made to prepare water/silica dry powder. As noted in Table 3A below, neither the 3 pph BXS-319 or the 5 pph BXS 320 could be mixed into water at all. Both samples were so hydrophobic that they floated on the surface of the water and resisted all attempts to mix them into the water to form a dry powder. However, the 1 pph silicone-treated sample BXS-318 could be mixed slowly into the water and formed a good dry powder at water/BXS-318 69.9/30.1 composition. The dry powder composition had a density of 0.52 grams/cc.

The thermal energy storage properties of the distilled water/BXS-318 silica dry powder were analyzed by DSC, and the results are summarized below in Table 3B.

TABLE 3A

EVALUATION OF PPG SILICAS IN H$_2$O/SILICA DRY POWDERS

| PPG IDENTIFICATION NUMBER | PPG's SILICA MODIFICATION(1) | H$_2$O/SILICA COMPOSITE WT % | APPARENT DENSITY GMS/CC | COMMENTS |
|---|---|---|---|---|
| I Milling, and 5 Versus 15 PPM Silicone Surface Treatment | | | | |
| 1. BXS-297 | Unmilled, 5 pph Silicone | — | — | Could not mix |
| 2. BXS-298 | Milled, BXS-297, 5 pph Silicone | — | — | " |
| 3. BXS-299 | Unmilled, 15 pph Silicone | — | — | " |
| 4. BXS-300 | Milled, BXS-299, 15 pph Silicone | — | — | " |
| II Normal Versus Low Salt ABS | | | | |
| 5. BXS-316 | "Normal" 0.5-1.5% Salt | 68.9/31.1 | 0.57 | Mixed easily |
| 6. BXS-317 | "Low" <0.1% Salt | 69.6/30.4 | 0.54 | Mixed easily |
| III Silicone Surface Treatment in ABS Silica | | | | |
| 7. BXS-318 | ABS, 1 pph Silicone | 69.9/30.1 | 0.52 | Mixed in slowly |
| 8. BXS-319 | ABS, 3 pph Silicone | —/— | — | Could not mix |
| 9. BXS-320 | ABS, 5 pph Silicone | —/— | — | Could not mix |
| IV Dimethyldichlorsilane Surface Treatment 0.01 ot 1.0 pph | | | | |
| 10. BXS-321 | ABS, 0.10 pph DMDCS | 71.0/29.0 | 0.56 | Mixed easily |
| 11. BXS-322 | ABS, 0.01 pph DMDCS | 69.3/30.7 | 0.54 | Mixed easily |
| 12. BXS-323 | ABS, 1.00 pph DMDCS | 68.7/31.3 | 0.59 | Mixed easily |
| V Calcining Heat Treatment to Remove Surface (OH) Groups | | | | |
| 13. BXS-324 | ABS Heat Treated to ~650° C. | 67.9/31.1 | 0.50 | Mixed easily |
| VI ABS Silica Modified to Increase Oil Absorption | | | | |
| 14. ABS-Lot H-18-9 | ABS Modified for Higher Oil Absorption | 73.0/27.0 | 0.43 | Mixed easily Higher H$_2$O/Silica Composite Wt. |
| VII Special Silica Base with 15 pph Silicone Surface Treatment | | | | |
| 15. BXS-245 | Special Base 15 pph Silicone | —/— | — | Could not mix |
| 16. BXS-258 | Special Base 15 pph Silicone | —/— | — | Could not mix |
| VIII Unmodified ABS Silica Control | | | | |
| 17. PPG ABS | Commercial Hydrophylic Silica | 68.9/31.1 | 0.51 | Easy to mix |

TABLE 3B

| Material | Tm °C. | Tc °C. | Tm-Tc °C. | AHf Cal/gm | Ahc Cal/gm |
|---|---|---|---|---|---|
| H$_2$O/BXS−318 (69.9/30.1) | 0.6 | −7.44 | 8.04 | 44.83 | 42.84 |
| H$_2$O/BXS−318 (69.9/30.1) | 0.6 | −7.52 | 8.12 | 44.32 | 42.08 |

EXAMPLE 4

The laboratory mixing procedure of Example 1 was used to prepare a series of water/silica dry powders using separately fumed silica from Cabot Corp. (Cab-O-Sil MS-7) and three different precipitated silicas, BXS- 316, 317 and 318 from PPG Industries as described in Examples 2 and 3. Free-flowing conformable powders were formed in each instance at water/silica ratios in the range of 60/40 to 70/30% by weight.

The melting temperatures, freezing temperature, difference between melting and freezing temperature, and heat of fusion and crystallization were determined by differential scanning calorimetry at a heating and cooling rate of 2° C./minute. The thermal storage values reported below in Table 4 are the average of at least two separate DSC measurements.

The Cab-O-Sil MS-7 fumed silica had a surface area of about 200 m²/gm, and an average particle diameter of 0.014 microns. The PPG precipitated silicas had a surface area of about 150–170 m²/gm, and primary particle sizes ranging from 0.016 to 0.22 microns.

TABLE 4

| Material | Tm °C. | Tc °C. | Tm-Tc °C. | AHf Cal/gm | Ahc Cal/gm |
|---|---|---|---|---|---|
| MS-7 | −1.86 | −14.81 | 12.61 | 28.77 | 25.77 |
|  | (Avg. of 3 analyses) | | | | |
| MS-7 | −2.06 | −14.87 | 12.61 | 24.50 | 24.85 |
|  | (Avg. of 3 analyses) | | | | |
| MS-7 | −0.80 | −16.83 | 16.02 | 38.54 | 37.89 |
|  | (Avg. of 2 analyses) | | | | |
| BXS-316 | +1.14 | −8.80 | 9.95 | 43.58 | 42.46 |
| BXS-317 | +0.60 | −7.48 | 8.08 | 44.58 | 42.46 |
| BXS-318 | +0.95 | −10.46 | 11.41 | 42.94 | 40.96 |
| (1 pph silicone resin surface-treated) | | | | | |

From the above data it is apparent that the water/silica/dry powders made with MS-7 fumed silica melt and freeze at a lower temperature, supercools more and stores and releases less thermal energy that the water/silica dry powder made with the precipitated silicas. These results are attributed to stronger hydrogen bonding of water molecules to the surface of the fumed silica which prevents melting and freezing at the usual temperature. The water/precipitated silica dry powder melts and freezes at about the same temperature as does 100% water (in the DSC analysis.).

EXAMPLE 5

The procedure of Example 1 was used to prepare NP-15/silica dry powder PCM using two different commercially available precipitated hydrophilic silicas from PPG Industries (ABS and 915), and two precipitated silicas from PPG Industries (BXS-245 and 258) surface-treated with about 15 pph of silicone resin to render them hydrophobic. The silicas which were surface treated to render them hydrophobic were precipitated silicas having a particle size of 0.022 microns and a surface area of 189 m²/gram and 114 m²/gram, respectively. The hydrophobic silicas were tested since this feature is desirable to prevent phase separation of the water and hydrocarbon PCM at temperatures above the melting temperature of the PCM.

During preparation of the dry powder mixes it was noted that the amount of silica required to achieve a free-flowing dry powder was slightly (but significantly) higher for the hydrophobic silicas than for the two "normal" hydrophilic silicas. Thermal energy storage properties were determined on each of the four dry powders, and on the starting NP-15 by differential scanning calorimeter analysis. A summary of DSC thermal energy storage data is shown below in Table 5.

TABLE 5

| Material | Tm °C. | Tc °C. | Tm-Tc °C. | AHf Cal/gm | Ahc Cal/gm |
|---|---|---|---|---|---|
| Hi-Sil 915 | 5.82 | 1.24 | 4.57 | 25.74 | 26.05 |
|  | (NP-15/915 (70.2/29.8% weight) | | | | |
| Hi-Sil ABS | 5.54 | 0.62 | 4.92 | 26.49 | 26.94 |
|  | (NP-15/ABS (70.2/29.8% weight) | | | | |
| BXS-245 | 5.60 | −1.30 | 6.90 | 21.82 | 22.56 |
|  | (NP-15/BXS-245 (64.5/35.5% weight). | | | | |
|  | Silicone surface waterproofing 15 pph | | | | |
| BXS-258 | 5.29 | 0.79 | 4.50 | 24.16 | 23.98 |
|  | (NP-15/BXS-258 (64.4/35.6% weight). | | | | |
|  | Silicone surface waterproofing 15 pph | | | | |
| NP-15 | 5.00 | 2.84 | 2.16 | 40.18 | 38.28 |
| 100% | −27.72 | −29.32 | 1.60 | 4.24 | 3.62 |

Note:
As shown in the above DSC data of the 100% NP-15, there is a small energy storage at about −28° C., and in the dry powders made therefrom. This is attributed to the presence of an "odd carbon atom" solid state transition present in this 15 carbon alkyl hydrocarbon.

160 grams of the NP-15/BXS-245 (64.5/35.5% weight) was placed in a sealed polyethylene bag and the material was placed in a freezer for 16 hours. The bag was then applied to a leg just above the knee with a temperature probe under the bag. Readings were started when the temperature probe reached its lowest reading and readings were stopped when the probe reached a temperature of 70° F. The test ran for a total of 160 minutes.

Further, an application test was performed in which about 300 grams (10.5 oz.) of the NP-15/ABS 70/30 silica dry powder was frozen by storing in a freezer for about four hours then placed on a counter top and temperature probes inserted underneath. Two other cold packs were tested at the same time, distilled water/ABS, and a commercial gel. As shown in FIG. 1, temperature was plotted versus time for each of the three test specimens. The abscissa units are in hours, and clearly show plateaus at constant temperature for both the NP-15/ABS and the water/ABS of more than 2½ hours. The commercial gel cold pack showed a continuous thermocline with no plateau time period and less than 1 hour in the desired temperature range.

EXAMPLE 6

The general procedure of Example 1 was modified to provide for heating a commercially available wax having a melting point of 60°–65° from Shell Oil Company of Houston, Tex. (Shellwax 300) (1000 grams) to a temperature of 125° C. by adding 0.1% (1 gram) of BHT antioxidant before adding any of the silica. The BXS-320, a precipitated silica from PPG Industries having a particle size of 0.022 microns, a surface area of 99 m²/gram and 5 pph silicone resin surface treatment was selected after testing higher and lower levels of silicone surface treatment for waterproofing capability.

Two separate batches of 100 grams of Shellwax 300 and 1 gram of BHT antioxidant were mixed with the BXS-320 silica. A soft gel was obtained at about Shellwax 300/BXS-320 77/23, a stiff gel at 75.8/24.2, and a free flowing dry powder at 67/33 (500 grams of BXS-320). An aliquot was tested for cold conformability by placing it in a freezer overnight, and was found the next day to remain a soft, conformable free flowing powder. Thermal energy storage was determined on a representative sample by DSC analysis at 2° C./minute rate of heating and cooling, with the results as shown in Table 6 below:

TABLE 6

| PCM | Tm °C. | Tc °C. | Tm-Tc °C. | AHf Cal/gm | Ahc Cal/gm |
|---|---|---|---|---|---|
| Shellwax 300/BXS-320 | 70.68 | 68.95 | 1.74 | 33.70 | 29.82 |

150 grams of commercial glycerine was added to one of the two 1500 gram batches and mixed into the dry powder. No phase separation was observed. An aliquot containing the 10% glycerine was tested for microwave heating capability in a small microwave oven and compared with a control of the second 1500 gram batch without the glycerine. The batch containing the 150 grams of glycerine was found to heat effectively to a temperature of about 100° C. in four minutes. The unmodified control showed only a slight warming in the same time in the microwave oven.

EXAMPLE 7

The general procedure of Example 1 as modified in Example 6 was used to prepare about 1500 grams of Shellwax 200 (a wax having a melting point of 52°-55° from Shell Oil Co.)/ABS silica (a precipitated from PPG Industries as described in Example 1) dry powder at about 70/30 weight percent. The Shellwax 200 melts and freezes at about 60° C., and in 100% concentration stores and releases 45-50 calories/gram. In this ABS silica composition, it was found that the silica went into the molten Shellwax 200 more rapidly than the BXS-320 of Example 6, and required less silica to reach the dry powder state (68/32% weight). DSC analysis of the dry powder confirmed that it stored and released the expected (70%) of the energy of the 100% linear paraffin.

DSC analysis of the Shellwax 200/ABS dry powder had thermal energy storage properties as shown in Table 7 below:

TABLE 7

| PCM | Tm °C. | Tc °C. | Tm-Tc °C. | AHf Cal/gm | Ahc Cal/gm |
|---|---|---|---|---|---|
| Shellwax 200/BXS-320 | 54.26 | 56.76 | 2.50 | 31.49 | 31.40 |

An application test was done in which the heat keeping capability of the Shellwax 200/ABS silica dry powder was compared to a commercial gel pack. Equal weights of each of the two hot pack systems was charged by heating in a microwave until both the Shellwax 200/ABS silica dry powder and the gel pack reached a temperature above 150° F., using three two-minute heating cycles of two minutes each. The packs were then transferred to a countertop, thermocouples inserted underneath each, and the time/temperature monitored (see FIG. 2). The Shellwax 200 had a plateau of temperature between 140 and 120 of about 2¼ hours. The commercial gel pack stayed in the same 140°-120° F. range on a pronounced thermocline for about ⅜ hours.

EXAMPLE 8

The general mixing procedure described in Example 1 was modified to include a mixing temperature of 100° C. that is well above the nominal 122° F. (60° C.) melting temperature of the polyethylene glycol 8,000 (PEG 8000). In contrast to lower molecular weight polyethylene glycols, the 8,000 molecular weight product has little or no hygroscopicity, and stores and releases about 42 cal/gram in melting and freezing (100% PCM). The polyethylene glycol has the added advantage that due to the polar character of the molecule (including terminal hydroxy groups) the PCM is inherently absorbing in the microwave energy spectrum and thus requires no additive to achieve microwave heating capability. About 1000 grams of PEG 8000 was placed in a stainless steel mixing tray, 1 gram of BHT antioxidant was added, and the contents heated to a temperature of 100° C. At this temperature ABS silica was incrementally added to form a dry powder at a composition of PEG-8000ABS silica of 70/30% weight.

The differential scanning calorimeter analysis of the neat (100%) polyethylene glycol 8000 and the PEG-8000/ABS silica dry powder showed the following thermal energy storage properties:

TABLE 8

| PCM | Tm °C. | Tc °C. | Tm-Tc °C. | AHf Cal/gm | Ahc Cal/gm |
|---|---|---|---|---|---|
| PEG-8000 Neat (100%) | 62.39 | 46.04 | 16.36 | 42.45 | 41.76 |
| PEG-8000/ ABS (70/30) | 60.96 | 44.28 | 16.69 | 28.59 | 25.64 |

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A composition, comprising, in combination a phase change material and finely divided silica particles, said phase change material being selected from the group consisting of quaternary ammonium halide linear alkyl hydrocarbons, fatty acids, alcohols and esters, said silica particles having particle sizes of about 0.005 to about 0.025 microns, and said phase change material having a melting point and freezing point of from about −20° to 140° C., said phase change material being present in an amount of about 50-75% by weight and said silica particles being present in an amount of about 25-50% by weight based upon the weight of said composition, said composition being in the form of a freely flowing powder mix.

2. The composition of claim 1 wherein said silica particles have a surface area of between about 50 m²/g and about 500 m²/g.

3. The composition of claim 4 wherein said silica particles are precipitated silica particles.

4. The composition of claim 5 wherein said silica particles have been rendered less hydrophilic, partially hydrophobic or hydrophobic by surface treatment with 1-15 parts per hundred by weight of a silicone resin.

5. The composition of claim 1 further comprising a polar compound present in an amount of 5-25% by weight based on the total weight of said composition, and wherein said composition may be heated by microwave energy.

6. The composition of claim 5 wherein said phase change material is a linear alkyl hydrocarbon and said polar compound is glycerine.

7. A composition, comprising, in combination a water phase change material and finely divided precipitated silica particles which are hydrophilic or only slightly hydrophobic and which have particle sizes of about 0.005 to about 0.025 microns.

8. The composition of claim 7 wherein said water phase change material is present in an amount of about 50-75% by weight and said silica particles are present in an amount of 25-50% by weight based upon the weight of said composition, said composition being in the form of a freely flowing powder mix.

9. The composition of claim 8 wherein said water phase change material is present in an amount of 60-70% by weight of the composition.

10. The composition of claim 9 wherein the apparent density is about 0.5 gm/cc, and said silica particles have a surface area of between about 50 $m^2/g$ and about 500 $m^2/g$.

* * * * *